United States Patent [19]
Murphy

[11] Patent Number: 5,374,506
[45] Date of Patent: Dec. 20, 1994

[54] AMINO ACID SEQUENCE FOR A FUNCTIONAL HUMAN INTERLEUKIN-8 RECEPTOR

[75] Inventor: Philip M. Murphy, Bethesda, Md.

[73] Assignee: The United States of America as represented by the Department of Health & Human Services, Washington, D.C.

[21] Appl. No.: 759,568

[22] Filed: Sep. 13, 1991

[51] Int. Cl.$^5$ .............................................. C07K 13/00
[52] U.S. Cl. .................................................... 530/350
[58] Field of Search ........................................ 530/351

[56] References Cited

PUBLICATIONS

Thomas et al 1991 J. Biol. Chem 266(23):14839–14841.
Lee et al. 1992 J. Biol Chem 267(23):16283–16287.
Julius, et al., "Molecular Characterization of a Functional cDNA Encoding the Serotonin 1c Receptor", Science, vol. 241, Jul. 29, 1988, pp. 558–564.
Bonner, et al., "Cloning and Expression of the Human and Rat m5 Muscarinic Acetylcholine Receptor Genes", Neuron, vol. 1, 000–000, Jul., 1988.
Thelen, et al., "Mechanism of neutrophil activation by NAF, a novel monocyte–derived peptide agonist", FJ Research Communication, pp. 2702–2706.
Devereux, et al., "A Comprehensive Set of Sequence Analysis Programs for the VAX", Nucleic Acids Research, vol. 12, No. 1, 1984, pp. 387–395.
Marilyn Kozak, "An Analysis of 5′–Noncoding Sequences from 699 Vertebrate Messenger RNAs", Nucleic Acids Research, vol. 15, No. 20, 1987, pp. 8125–8133.
Samanta, et al., "Identification and Characterization of Specific Receptors for Monocyte–Derived Neutrophil Chemotactic Factor (MDNCF) On Human Neutrophils, The Journal of Experimental Medicine, vol. 169, Mar. 1989, pp. 1185–1189.
Kyte, et al., "A Simple Method for Displaying the Hydropathic Character of a Protein", J. Mol. Biol. (1982), 157, pp. 105–132.
Moser, et al., "Neutrophil-Activating Properties of the Melanoma Growth-Stimulatory Activity", J. Exp. Med. vol. 171, May 1990, pp. 1797–1802.
Leonard, et al., "Leukocyte Specificity and Binding of Human Neutrophil Attractant/Activation Protein-1", The Journal of Immunology, vol. 144, No. 4, Feb. 5, 1990, pp. 1323–1330.
Boulay, et al., "Synthesis and Use of a Novel N-Formyl Peptide Derivative to Isolate A Human N-Formyl Peptide Receptor cDNA", Biochemical and Biophysical Research Communications, vol. 168, No. 3, May 16, 1990, pp. 1103–1109.
Murphy, et al., "Functional Expression of the Human Formyl Peptide Receptor in Xenopus Oocytes Requires a Complemental Human Factor", The Journal of Biol Chem., vol. 266, No. 19, Jul. 5, 1991, pp. 12560–12567.
Murphy, et al., "Characterization of Human Phagocytic Cell Receptors for C5A and Platelet Activating Factor Expressed in Xenopus Ooctyes", The Journal of Immunology, vol. 145, No. 7, Oct. 1, 1990, pp. 2227–2234.
Wolpe, et al., "Macrophage Inflammatory Proteins 1 and 2: Members of a Novel Superfamily of Cytokines", The FASEB Journal, vol. 3, Dec. 1989, pp. 2565–2573.
Malech, et al., "Asparagine-Linked Oligosaccharides on Formyl Peptide Chemotactic Receptors of Human Phagocytic Cells", The Journal of Biol. Chem., vol. 260, No. 4, Feb. 25, 1985, pp. 2509–2514.
Sanger, et al., "DNA Sequencing with Chain-Ter-
(List continued on next page.)

Primary Examiner—Robert J. Hill, Jr.
Assistant Examiner—K. Cochrane Carlson
Attorney, Agent, or Firm—Townsend and Townsend Khourie and Crew

[57] ABSTRACT

A cDNA clone from HL60 neutrophils, designated p2, which encodes a human interleukin-8 receptor. This IL-8 receptor can be expressed in oocytes or transfected host cells. This receptor has 77% amino acid identity with a second human neutrophil receptor isotype that also binds IL-8. It also exhibits 69% amino acid identity with a protein reported to be an N-formyl peptide receptor from rabbit neutrophils.

3 Claims, 11 Drawing Sheets

PUBLICATIONS minating Inhibitors", Proc. Natl. Acad. Sci, USA, vol. 74, No. 12, Dec., 1977, pp. 5463–5467.

Holmes, et al., "Structure and Functional Expression of a Human Interleukin-8 Receptor", Science, vol. 253, pp. 1278–1280.

Gerard, et al., "The Chemotactic Receptor for Human C5a Anaphylatoxin", Nature, vol. 349, Feb. 14, 1991, pp. 614–617.

Thomas et al., "Molecular Cloning of the fMet–Leu-Phe Receptor from Neutrophils", The Journal of Biol. Chem., vol. 265, No. 33, Nov. 25, 1990, pp. 20061–20064.

Walz, et al., "Effects of the Neutrophil-Activating Peptide NAP-2, Platelet Basic Protein, Connective Tissue-Activating Peptide III, and Platelet Factor 4 on Human Neutrophils", J. Exp. Med., vol. 170, Nov. 1989, pp. 1745–1750.

Sullivan, et al., "Acquisition of Formyl Peptide Receptors During Normal Human Myeloid Differentiation", 1987, pp. 1222–1224.

Yokoyama, et al., "Adaptive Evolution of G-Protein Coupled Receptor Genes", Mol. Biol. Evol. vol. 6, 1989, pp. 342–353.

Appella, et al., "Determination of the Primary and Secondary Structure of Nap-1/IL-8 and a Monocyte Chemoattractant Protein, MCP-1/MCAF", pp. 405–417.

Murphy, et al., "Cloning of Complementary DNA Encoding a Functional Human Interleukin-8 Receptor", Science, vol. 253, Sep. 13, 1991, pp. 1280–1283.

Murphy, et al, "Characterization of Phagocyte P2 Nucleotide Receptors Expressed in Xenopus Oocytes", The Journal of Biol Chem., vol. 265, Jul. 15, 1990, pp. 11615–11621.

Moser, et al., "Neutrophil-Activating Peptide 2 and Gro/Melanoma Growth-Stimulatory Activity Interact with Neutrophil-Activating Peptide 1/Interleukin 8 Receptors on Human Neutrophils", The J of Biol. Chem, vol. 266, No. 16, Jun. 5, 1991, pp. 10666–10671.

Besemer, et al. "Specific Binding, Internatization, and Degradation of Human Neutrophil Activating Factor by Human Polymorphonuclear Leukocytes", The Journal of Biol. Chem., vol. 264, Oct. 15, 1989, pp. 17409–17415.

Grob, et al., "Characterization of a Receptor for Human Monocyte-derived Neutrophil Chemotactic Factor/Interleukin-8", The Journal of Biol. Chem., vol. 265, No. 14, May 15, 1990, pp. 8311–8316.

FIG. 3A

```
        20                    40                      60
IL-8R  MESDSFE--DFWK-GED-LSNYSSSTLPPFLLDAAPCEPESLEINKYFVIIYALVFLLSLLGNSLVMLVILYS
F3R    MEVNVWNMTDLWTWFEDEFANAT--GMPPVEKDYSPCLVVTQTLNKYVVVVIYALVFLLSLLGNSLVMLVILYS
FPR    MET---NSS---------LPTNISGTPAVSAGYLFLDIITYLVFAVTFVLGVLGNGLVIWVAGF-
                                                    ├──────── I ────────┤

80                100                  120                  140
       RVGRSVTDVYLLNLALA-DLLFALTLPIWAASKVNG--WIFGTFLCKVVSLLKEVNFYSGILLACISVDRYLAIVHATRTL
       RSNRSVTDVYLLNLAMAPAFCPDHA---YLGR-LQGKRLDFRTPLCKVVSLVKEVNFYSGILLACISVDRYLAIVQSTRTL
       RMTHTVTTISYLNLAVA-DFCFTSTLPFFMVRKAMGGHWPFGWFLCKFLFTIVDINLFGSVFLIALIALDRCVCVLHPVWTQ
       ├────── II ──────┤              ├──────── III ────────┤
```

FIG. 3B

```
          ┌──── IV ────┐
         160          180                 200
TQKR-YLVKFICLSIWGLSLLLALPVLLFRRTVYSSNVS-PAC---YEDMGNNTANWR---
        | ||||||||| |||||  |||||||   |||  |||   |||||
TQKR-HLVKFICLGIWALSLILSLPFFLFRQ--VFSPNNSSPVC---YEDLGHNTAKWC---
                                                |
NHRTVSLAKKVIIGPWVMALLLTLPVIIRVTTVPGKTGTVA-CTFNFSPWTNDPKERINV

┌──── V ────┐                   ┌──── VI ────┐
         220          240                 260
----MLLR-ILPQSFGFIVPLLIMLFCYGFTLRTLFKAHMGQKHRAMRVIFAVVLIFLLCWLPYNLVLLADTLMRTQ
       |  ||| | ||| ||||||||||||||  |||||||||||||||||||||||||||||||||||||||
----TVLR-ILPHTFGFILPLLVMLFCYGFTLRTLFQAHMGQKHRAMRVIFAVVLIFLLCWLPYNLVLLADTLMRTH
              |  ||  ||  |                                  |
AVAMLTV-RGIIRFIIGFSAPMSIVAVSYGLIATKIHKQGLIKSSRPLRVLSFVAAAFFLCWSPYQVVALIATVRIRE
```

FIG. 3C

```
                                    VII
        280              300              320              340
VIQETCERRNHIDRALDATEILGILHSCLNPLIYAFIGQKFRHGLLKILAI---HGLISKDSLPKDSRPSFVGSSSGHTSTTL 355
VIQETCQRRNELDRALDATEILGFLHSCLNPIIYAFIGQNFRNGFLKMLAA---RGLISKEFLTRHRVTSYTSSSTNVPSNL 354
LLQGMY---KEIGIAVDVTSALAFFNSCLNPMLYVFMGQDFRERLIHALPASLERALTEDSTQTSDTATNSTLPSAEVALQAK 350
```

FIG. 5A

```
  1  GTCAGGATTT AAGTTTACCT CAAAAATGGA AGATTTTAAC ATGGAGAGTG
 51  ACAGCTTTGA AGATTTCTGG AAAGGTGAAG ATCTTAGTAA TTACAGTTAC
101  AGCTCTACCC TGCCCCCTTT TCTACTAGAT GCCGCCCCAT GTGAACCAGA
151  ATCCCTGGAA ATCAACAAGT ATTTTGTGGT CATTATCTAT GCCCTGGTAT
201  TCCTGCTGAG CCTGCTGGGA AACTCCCTCG TGATGCTGGT CATCTTATAC
251  AGCAGGGTCG GCCGCTCCGT CACTGATGTC TACCTGCTGA ACCTAGCCTT
301  GGCCGACCTA CTCTTTGCCC TGACCTTGCC CATCTGGGCC GCCTCCAAGG
351  TGAATGGCTG GATTTTTGGC ACATTCCTGT GCAAGGTGGT CTCACTCCTG
401  AAGGAAGTCA ACTTCTATAG TGGCATCCTG CTACTGGCCT GCATCAGTGT
451  GGACCGTTAC CTGGCCATTG TCCATGCCAC ACGCACACTG ACCCAGAAGC
```

FIG. 5B

```
501  GCTACTTGGT CAAATTCATA TGTCTCAGCA TCTGGGGTCT GTCCTTGCTC
551  CTGGCCCTGC CTGTCTTACT TTTCCGAAGG ACCGTCTACT CATCCAATGT
601  TAGCCCAGCC TGCTATGAGG ACATGGGCAA CAATACAGCA AACTGGCGGA
651  TGCTGTTACG GATCCTGCCC CAGTCCTTTG GCTTCATCGT GCCACTGCTG
701  ATCATGCTGT TCTGCTACGG ATTCACCCTG CGTACGCTGT TTAAGGCCCA
751  CATGGGGCAG AAGCACCGGG CCATGCGGGT CATCTTTGCT GTCGTCCTCA
801  TCTTCCTGCT TTGCTGGCTG CCCTACAACC TGGTCCTGCT GGCAGACACC
851  CTCATGAGGA CCCAGGTGAT CCAGGAGACC TGTGAGCGCC GCAATCACAT
901  CGACCGGGCT CTGGATGCCA CCGAGATTCT GGGCATCCTT CACAGCTGCC
951  TCAACCCCCT CATCTACGCC TTCATTGGCC AGAAGTTTCG CCATGGACTC
```

FIG. 5C

```
1001  CTCAAGATTC TAGCTATACA TGGCTTGATC AGCAAGGACT CCCTGCCCAA
1051  AGACAGCAGG CCTTCCTTTG TTGGCTCTTC TTCAGGGCAC ACTTCCACTA
1101  CTCTCTAAGA CCTCCTGCCT AAGTGCAGCC CGTGGGGTTC CTCCCTTCTC
1151  TTCACAGTCA CATTCCAAGC CTCATGTCCA CTGGTTCTTC TTGGTCTCAG
1201  TGTCAATGCA GCCCCCATTG TGGTCACAGG AAGCAGAGGA GGCCACGTTC
1251  TTACTAGTTT CCCTTGCATG GTTTAGAAAG CTTGCCCCTGG TGCCTCACCC
1301  CTTGCCATAA TTACTATGTC ATTTGCTGGA GCTCTGCCCA TCCTGCCCCT
1351  GAGCCCATGG CACTCTATGT TCTAAGAAGT GAAAATCTAC ACTCCAGTGA
1401  GACAGCTCTG CATACTCATT AGGATGGCTA GTATCAAAAG AAAGAAAATC
1451  AGGCTGGCCA ACGGGATGAA ACCCTGTCTC TACTAAAAAT ACAAAAAAAA
1500  AAAAAAAAAA
```

FIG. 6

5'-GACGTCTACCTGCTGAACCTGGCCATGGCACCTGCTTTT-3'

AMINO ACID SEQUENCE FOR A FUNCTIONAL HUMAN INTERLEUKIN-8 RECEPTOR

BACKGROUND OF THE INVENTION

1. Field of the Invention

The invention relates to identification and characterization of a human interleukin-8 receptor which also binds gro. In another aspect, it relates to stable expression of functionally active IL-8 receptor in host cells.

2. Background Information

Stimulation of neutrophils with IL-8, NAP-2 or gro causes mobilization of intracellular calcium stores and elicits motile, secretory, and metabolic responses that are critical to the role of the neutrophil in host defenses. See B. Moser, I. Clark-Lewis, R. Zwahlen, M. Baggiolini, *J. Exp. Med.* 171, 1797 (1990); A. Walz, B. Dewald, V. von Tscharner, M. Baggiolini, ibid. 170, 1745 (1989); and M. Thelen et al., *FASEB J.* 2, 2702 (1988). IL-8 is an inflammatory cytokine that activates neutrophil chemotaxis, degranulation and the respiratory burst, the means by which neutrophils attack pathogens in the body. Neutrophils express receptors for IL-8 that are coupled to guanine nucleotide binding proteins (G-proteins); binding of IL-8 to its receptor induces the mobilization of intracellular calcium stores. IL-8, also known as neutrophil activating protein-1 or NAP-1, is a potent chemoattractant for neutrophils that is produced by many cell types in response to inflammatory stimuli. See J. J. Oppenheim, *Prog. Clin. Biol. Res.* 349, 405 (1990). This IL-8 receptor has 77% amino acid identity with a second human neutrophil receptor isotype that also binds IL-8 (Genentech, *FASEB*, April 1991).

IL-8 is structurally and functionally related to several members of the macrophage inflammatory protein-2 (or MIP-2) family of cytokines. These include MIP-2, gro (or melanoma growth-stimulatory activity), and NAP-2. See S. D. Wolpe and A. Cerami, *FASEB J.* 3, 2565 (1989); B. Moser, I. Clark-Lewis, R. Zwahlen, M. Baggiolini, *J. Exp. Med.* 171, 1797 (1990); and A. Walz, B. Dewald, V. von Tscharner, M. Baggiolini, ibid. 170, 1745 (1989). High affinity binding sites for IL-8 have been found on transformed myeloid precursor cells such as HL60 and THP-1 as well as on neutrophils. See B. Moser, C. Schumacher, V. von Tscharner, I. Clark-Lewis, M. Baggiolini, *J. Biol. Chem.* 266, 10666 (1991); J. Besemer, A. Hujber, B. Kuhn, *J. Biol. Chem.* 264, 17409 (1989); P. M. Grob et al., ibid. 265, 8311 (1990); A. K. Samanta, J. J. Oppenheim, K. Matsushima, *J. Exp. Med.* 169, 1185 (1989); E. J. Leonard et al., *J. Immunol.* 144, 1323 (1989). NAP-2 and gro compete with IL-8 for binding to human neutrophils suggesting that they interact with the same receptors. See B. Moser, C. Schumacher, V. von Tscharner, I. Clark-Lewis, M. Baggiolini, *J. Biol. Chem.* 266, 10666 (1991).

Functional expression in the Xenopus oocyte has established the identity of cDNA clones encoding rabbit and human forms of another peptide chemoattractant receptor on neutrophils, the N-formyl peptide receptor. See K. M. Thomas, H. Y. Pyun, J. Navarro, *J. Biol. Chem.* 265, 20061 (1990); and F. Boulay, M. Tardif, L. Brouchon, P. Vignais, *Biochem. Biophys. Res. Commun.* 168, 1103 (1990). Yet the amino acid sequence of the rabbit form of the receptor (originally designated F3R) is only 28% identical with that of the human form (designated in this paper as FPR); this is far greater than the differences between species reported for all other G protein-coupled receptors. See T. I. Bonner, A. C. Young, M. R. Brann, N. J. Buckley, *Neuron* 1, 403 (1988); and S. Yokoyama, K. E. Eisenberg, A. F. Wright, *Mol. Biol. Evol.* 6, 342 (1989).

By cloning the complementary DNA sequence encoding the human interleukin 8 receptor (IL8R), the primary structure of this receptor can be established and its role in the inflammatory response can be further investigated. Such studies could potentially lead to the design of new anti-inflammatory agents.

SUMMARY OF THE INVENTION

It is an object of the present invention to isolate and characterize human interleukin-8 receptors.

The present invention relates to a cDNA clone from HL60 neutrophils, designated p2, which encodes an IL-8 receptor having an amino acid sequence as shown in FIG. 3.

The present invention further relates to the IL-8 receptor itself which has intracellular calcium store mobilizing properties and ligand binding properties.

Furthermore, the invention relates to an oocyte expressing IL-8 receptors produced by injecting a cRNA molecule transcribed from the cDNA clone, p2. Additionally, the present invention relates to a method of producing the IL-8 receptor in an oocyte.

Furthermore, the present invention relates to a host cell stably transfected with the cDNA clone, p2. In addition, the present invention relates to a method of producing the IL-8 receptor in a host cell.

In addition, the present invention relates to a method of detecting the presence or absence of a DNA segment encoding the IL-8 receptor in a sample by contacting the sample with a DNA probe having at least a portion of the sequence of the cDNA clone, p2.

Various other objects and advantages of the present invention will become apparent from the following figures and description of the invention.

BRIEF DESCRIPTION OF THE DRAWINGS

FIG. 1(A) shows translation of p2 cRNA by rabbit reticulocyte lysate (lane 2) compared with control lysate to which no RNA was added (lane 1). Red blood cell membrane proteins were used as molecular mass standards indicated in kilodaltons (kD) at the left. The gel was exposed to XAR-2 film for 12 hours.

FIG. 1(C) shows p2 mRNA distribution. The blot of RNA from neutrophils FIG. 1(B) was prepared separately from 10 μg of total cellular RNA FIG. 1(C). The other lanes derive from a single blot containing total cellular RNA from peripheral blood T lymphocytes activated with phytohemagglutinin (PHA-T, 5 μg), THP-1 cells (5 μg) and Jurkat cells (3 μg). The lane marked HL60 contains 10 μg of polyadenylated [poly (A)+] RNA from undifferentiated HL60 cells. The arrow indicates the location of a faint band of RNA from THP-1 cells. Both blots were hybridized under identical conditions with the same p2 probe and were washed at 68° C. in 0.1 X SSPE for 1 hour. Blots were exposed to XAR-2 film in a Quanta III cassette at −80° C. for 5 days. Results with 3 independent HL60 cell preps and 2 separate THP-1 and neutrophil blots were identical.

FIG. 2(A) shows signal transduction by the IL-8 receptor. Four days after injection with 5 ng of p2 cRNA, oocytes were stimulated with the indicated concentration of IL-8 and calcium efflux was measured. Data derive from five replicate determinations per point and are representative of three separate experiments.

FIG. 2(B) shows binding of [$^{125}$I]-IL-8 to oocytes expressing a functional IL-8 receptor. Total (●) and non-specific binding (○) was determined by incubating oocytes injected with p2 cRNA with the indicated concentration of radioligand in the absence or presence of unlabeled IL-8 (1 μM), respectively. The data shown are the mean±SEM of triplicate determinations per point and are representative of two separate experiments. Nonspecific binding was subtracted from total binding to determine specific binding (□). C5a (1 μM) did not displace [$^{125}$I]-IL-8 from oocytes injected with p2 cRNA. Specific binding of [$^{125}$I]-IL-8 by oocytes injected with water was undetectable.

FIG. 2(C) shows ligand selectivity of the IL-8 receptor. Three days after injection with 5 ng of p2 cRNA, oocytes were stimulated with the indicated concentration of IL-8 (●), gro (□), NAP-2 (○), FMLP (●) or C5a (△), and calcium efflux activity was measured. Data derive from eight replicate determinations per point. The response of oocytes injected with 50 ng of HL60 neutrophil RNA to FMLP (1 μM) or C5a (500 nM) was 51±3 and 16±5%, respectively. The response of oocytes injected with 5 ng of an irrelevant cRNA encoding the rat serotonin 1c receptor was negligible for each of the five ligands; the response to the relevant ligand, serotonin (1 μM), was 34±3% (n=6). See D. Julius, A. B. McDermott, R. Axel, T. M. Jessell, *Science* 241, 558 (1988). In (A) and (C) basal amounts of calcium efflux and calcium uptake were similar among all experimental conditions.

FIGS. 3(A)–3(C) shows the primary structure of a human IL-8 receptor (IL-8R) (SEQ ID NO:1) and its alignment with that of the reported rabbit (F3R) (SEQ ID NO:2) and human (FPR) (SEQ ID NO:3) N-formyl peptide receptors. Vertical bars indicate identical residues for each adjacent sequence position. Shaded boxes indicate the location of predicted membrane spanning segments I through VII as determined by the Kyte-Doolittle algorithm. See J. Kyte and R. F. Doolittle, *J. Molec. Biol.* 157, 105 (1982). Open boxes designate predicted sites for N-linked glycosylation. Arabic numbers above the sequence blocks enumerate the IL-8 receptor sequence and are left justified. Dashes indicate gaps that were inserted to optimize the alignment. Abbreviations for the amino acid residues are: A, Ala; C, Cys; D, Asp; E, Glu; F, Phe; G, Gly; H, His; I, Ile; K, Lys; L, Leu; M, Met; N, Asn; P, Pro; Q, Gly; R, Arg; S, Ser; T, Thr; V, Val; W, Trp; and Y, Tyr.

FIGS. 5(A)–5(C) shows the nucleotide sequence of p2 (SEQ ID NO:4), having a length of 1510 nucleotides.

FIG. 6 shows the oligonucleotide probe (SEQ ID NO:5) corresponding to nucleotides 238 to 276 of the cDNA sequence of F3R.

DESCRIPTION OF THE PREFERRED EMBODIMENTS

Figure 1A:
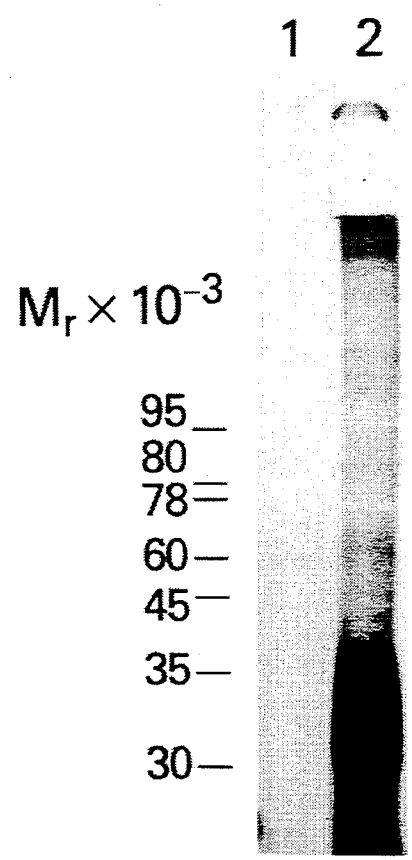
FIGS. 1A–1C shows the results of in vitro translation of p2 and distribution of p2 mRNA in various cell types.

The present invention relates to a human IL-8 receptor and its encoding cDNA clone, designated p2. This receptor is a newly identified human homologue of F3R.

The present invention further relates to a cRNA molecule transcribed from the cDNA clone, p2. The present invention also relates to an interleukin-8 receptor which is also a gro receptor and has greater than 77% homology with the amino acid sequence shown in FIGS. 3(A)–3(C).

Furthermore, the present invention relates to an oocyte, such as a *Xenopus laevis* oocyte, which expresses a functionally active form of the IL-8 receptor, when it is injected with a cRNA molecule transcribed from the cDNA clone, p2. The invention also relates to the method of injecting p2 into individual oocytes using standard techniques and experimental conditions which would be understood by one skilled in the art.

Additionally, the present invention relates to a recombinant DNA molecule and to a host cell transfected therewith which expresses a functionally active form of the IL-8 receptor. Using standard methodology well known in the art, a recombinant DNA molecule comprising a vector and a cDNA segment, p2, can be constructed using methods known in the art without undue experimentation. The transfected host cell can be cultured, and the expressed protein can be isolated and obtained in a substantially pure form using methods known in the art. COS cells (monkey kidney cells) or NIH 3T3 or other eukaryotic host cells conventionally used in the art to express inserted cDNA may also be used. As a vector, pcDNAI or pCLNXneo can be used as well as other vectors conventionally used in the art.

The invention further relates to the IL-8 receptor's intracellular calcium store mobilizing properties and ligand binding properties. Specifically, the IL-8 receptor encoded by p2 has been shown to bind both IL-8 and gro and to exhibit calcium flux as a result of such binding.

The invention also relates to a method of detecting the presence or absence of a DNA segment encoding the IL-8 receptor or a related receptor from the MIP-2 family in a sample by contacting the sample with a p2 probe having at least a portion of the cDNA clone. The method is performed under conditions such that hybridization between the probe and the DNA segment from the sample occurs. This hybridization can be detected by assaying for the presence or absence of a complex formed between the probe and the DNA segment. The techniques and experimental conditions used would be understood by one skilled in the art.

The invention also relates to a method of screening ligands of the IL-8 receptor by measuring binding affinity and calcium flux resulting from the binding of the ligand to the receptor expressed in the oocyte or the host cell. The techniques and experimental conditions used would understood by one skilled in the art.

The invention also relates to a gene therapy treatment by which an individual with a condition relating to a deficiency of IL-8 receptor might be treated by administering to the individual DNA encoding the IL-8 receptor in a form such that the DNA would alleviate the deficiency of IL-8 receptor. Conventional gene therapy techniques understood by one skilled in the art could be used. However, there is so far no evidence which points to the existence of such a condition of IL-8 receptor deficiency.

The following non-limiting examples are provided to further describe the present invention.

EXAMPLES

Example 1

The DNA segment which encodes the IL-8 receptor was obtained in the form of the cDNA clone, p2, using the following techniques and conditions.

cDNA libraries were constructed in the vector Uni-ZAP (Stratagene, La Jolla, Calif.) from 2-kb and 3.5-kb fractions of poly(A)+RNA from HL60 neutrophils that had been separated on a sucrose gradient as described in P. M. Murphy, E. K. Gallin, H. L. Tiffany, *J. Immunol.* 145, 2227 (1990).

Approximately $3 \times 10^5$ plaque-forming units (pfu) from the 2-kb library were screened with the $^{32}$P-labeled F3R oligonucleotide probe.

Both the 2-kb ($3 \times 10^5$ pfu) and the 3.5-kb ($10^6$ pfu) libraries were rescreened under conditions of low stringency with a $^{32}$P-labeled probe of p2 cDNA synthesized from random primers. The final wash was for one hour at 55° C. in 5 X SSPE (1 X SSPE contains 150 mM NaCl, 10 mM NaH$_2$PO$_4$, and 1 mM Na$_2$EDTA, pH 7.4).

The DNA sequence was determined with sequence-based oligonucleotides (17 bases) by the dideoxynucleotide chain termination method. See F. Sanger, S. Nicklen, A. R. Coulson, *Proc. Natl. Acad. Sci. U.S.A.* 74, 5463 (1977).

DNA sequences were analyzed using software from the University of Wisconsin Genetics Computer Group on a Cray supercomputer maintained by the National Cancer Institute Advanced Scientific Computing Laboratory, Frederick Cancer Research Facility, Frederick, Md. See J. Devereux, P. Haeberli, O. Smithies, *Nucleic Acids Res.* 12, 389 (1984).

An oligonucleotide probe corresponding to nucleotides 238 to 276 of the cDNA sequence of F3R (FIG. 6) was hybridized to cDNA libraries made from RNA from the promyelocytic leukemia cell line HL60 grown for two days in the presence of dibutyryl cyclic adenosine monophosphate (750 µM), a treatment that induces a neutrophil-like phenotype. See K. M. Thomas, H. Y. Pyun, J. Navarro, *J. Biol. Chem.* 265, 20061 (1990). Seven clones that encoded an identical gene product were isolated. The longest of these, designated p2, was sequenced on both strands (FIGS. 5(A)–5(C)). Confirmatory sequences were obtained from the other clones. A 1065-bp (base pair) open reading frame begins with the sequence AACATGG which conforms to the Kozak consensus criteria for translation initiation sites. See M. Kozak, *Nucleic Acids Res.* 15, 8125 (1987). A 24 bp poly(A) tail is found at the end of a 405 bp 3'-untranslated region.

The cDNA clone, p2, which was obtained was characterized and found to encode the IL-8 receptor.

Example 2 p2 cRNA was synthesized by in vitro transcription with T3 RNA polymerase of a pBluescript construct that had been cleaved with Xho I. p2 cRNA (500 ng) was incubated for 30 min at 30° C. with rabbit reticulocyte lysate and [$^{35}$S]-methionine in a 25 µl reaction volume (Promega, Madison, Wisc.). Labeled proteins (40% of the yield) were then separated by SDS-polyacrylamide gel electrophoresis [10% gels (Novex, Encinitas, Calif.)]. The gel was stained with Coomassie blue, fixed, impregnated with Fluoro-Hance (Research Products International, Mount Prospect, Ill.), and dried before autoradiography.

It has been found that RNA synthesized in vitro from p2 cDNA (p2 cRNA) directed the synthesis of a polypeptide of 32 kilodaltons in vitro (FIG. 1A). This is the size of the deglycosylated native N-formyl peptide receptor as well as the size found for FPR protein synthesized in vitro. See H. L. Malech, J. P. Gardner, D. F. Heiman, S. A. Rosenzweig, *J. Biol. Chem.* 260, 2509 (1985). It is known that binding sites for N-formyl peptides are expressed in mature but not in immature myeloid cells. See R. Sullivan, J. D. Griffin, H. L. Malech, *Blood* 70, 1222 (1987). It is also known that expression of RNA for FPR is restricted to mature myeloid cells as well.

Figure 1B:
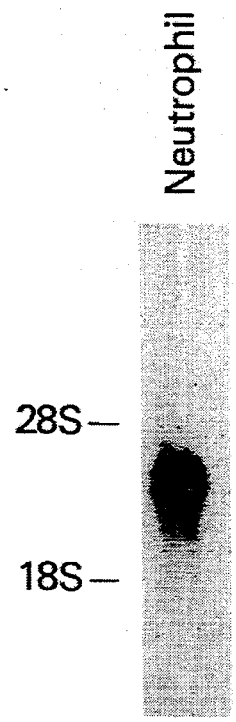
Figure 1C:
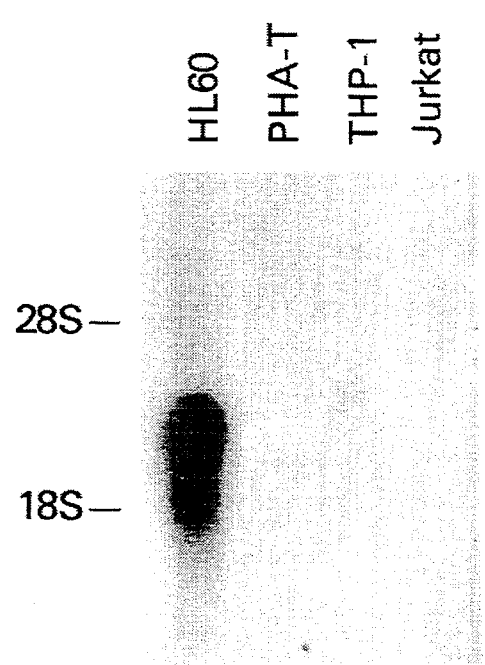

In contrast, it has been found that when p2 was used as a probe, it hybridized with a single 3-kb band on blots of RNA from the myeloid precursor cell lines HL60 and THP-1, and from normal blood-derived human neutrophils (FIG. 1(B)), but not from peripheral blood T lymphocytes or Jurkat cells (FIG. 1(C)). (For a description of RNA preparation and blot hybridization, see P. M. Murphy and H. L. Tiffany, *J. Biol. Chem.* 265, 11615 (1990).) This pattern of expression of p2 RNA is more like the distribution of IL-8 binding sites than N-formyl peptide binding sites. See J. Besemer, A. Hujber, B. Kuhn, *J. Biol. Chem.* 264, 17409 (1989); P. M. Grob et al., ibid. 265, 8311 (1990); A. K. Samanta, J. J. Oppenheim, K. Matsushima, *J. Exp. Med.* 169, 1185 (1989); and E. J. Leonard et al., *J. Immunol.* 144, 1323 (1989).

Example 3

The materials and methods used for the calcium efflux assay were as described in P. M. Murphy, E. K. Gallin, H. L. Tiffany, *J. Immunol.* 145, 2227 (1990). Oocytes were microinjected with RNA samples in a total volume of 50 nl per oocyte 3 days after harvesting and were then incubated at 20° to 23° C. for 2 to 4 days. Oocytes were then incubated with $^{45}$Ca$^{2+}$ [50 µCi/ml (ICN Biomedicals, Costa Mesa, Calif.)] for 3 hours. After ten washes with medium, individual oocytes were stimulated with ligand in wells of a 96-well tissue culture plate containing 100 µl of medium. Three 100 µl samples of the incubation medium were collected and analyzed by liquid scintillation counting: a) the final 100 µl wash (20 min) before application of ligand; b) fluid containing the stimulus, removed after a 20 min incubation with the oocyte; and c) the oocyte solubilized in SDS (1%) in medium 20 min after stimulation. Data are presented as the mean±standard error of the mean (SEM) of the percent of loaded $^{45}$Ca$^{2+}$ that was released by individual oocytes in response to the stimulus, or $[(b-a) \div (b+c)] \times 100$. FMLP and recombinant human C5a was from Sigma, St. Louis, Mo. Recombinant human IL-8 was from Genzyme, Boston, Mass. Recombinant human NAP-2 was from Bachem, Philadelphia, Pa.

IL-8 was iodinated to a specific activity of 260 Ci/mmole as described in H. L. Malech, J. P. Gardner, D. F. Heiman, S. A. Rosenzweig, *J. Biol. Chem.* 260, 2509 (1985). The radioligand was qualified by binding to human neutrophils. Single oocytes were incubated with [$^{125}$I]-IL-8 for 30 min on ice in 10 μl binding buffer (Hanks balanced salt solution with 25 mM HEPES, 1% bovine serum albumin, pH 7.4). Unbound ligand was removed by pelleting the oocyte through 300 μl F50 silicone fluid (General Electric, Waterford, N.Y.). The tube was quick-frozen and gamma emissions from the amputated tips were counted.

Figure 2A:
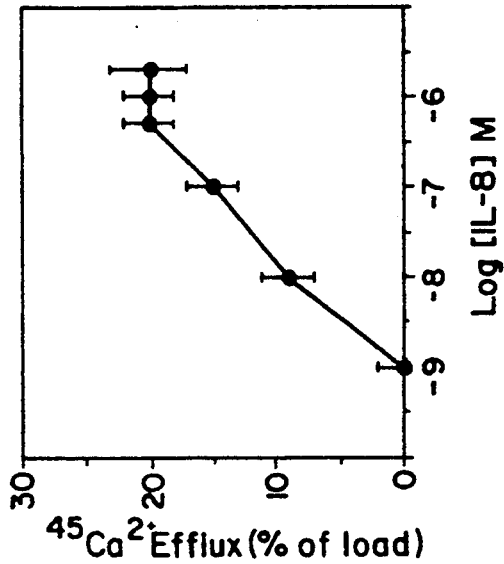
FIGS. 2(A)–2(C) shows the expression of a human IL-8 receptor in Xenopus oocytes.
Figure 2B:
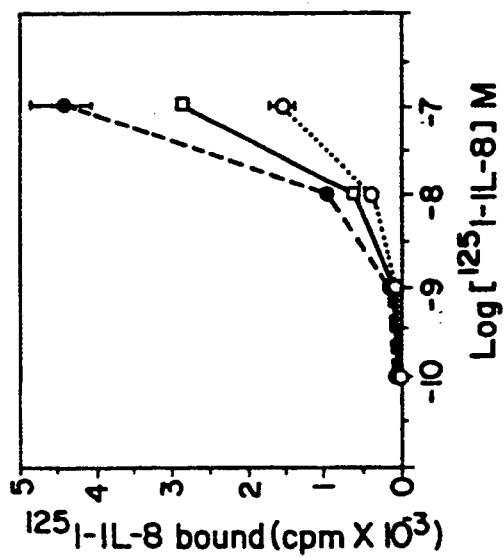

When Xenopus oocytes were injected with p2 cRNA, they mobilized intracellular calcium in response to IL-8 with an $EC_{50}$ of 20 nM (FIG. 2A), but did not respond to N-formyl methionyl-leucylphenylalanine (FMLP). This value is approximately 20-fold higher than that reported for human neutrophils with recombinant human IL-8. See B. Moser, I. Clark-Lewis, R. Zwahlen, M. Baggiolini, *J. Exp. Med.* 171, 1797 (1990). The receptor specifically bound IL-8 over the same concentration range as for stimulation of calcium flux (FIG. 2B). Since specific binding did not saturate at the highest concentration of radioligand that could be meaningfully tested, a dissociation constant could not be determined. Thus the receptor encoded by p2, when expressed in the oocyte, appears to bind IL-8 with a lower affinity than do neutrophil binding sites for IL-8. See B. Moser, C. Schumacher, V. von Tscharner, I. Clark-Lewis, M. Baggiolini, *J. Biol. Chem.* 266, 10666 (1991); J. Besemer, A. Hujber, B. Kuhn, *J. Biol. Chem.* 264, 17409 (1989); P. M. Grob et al., ibid. 265, 8311 (1990); A. K. Samanta, J. J. Oppenheim, K. Matsushima, *J. Exp. Med.* 169, 1185 (1989); and E. J. Leonard et al., *J. Immunol.* 144, 1323 (1989).

Figure 2C:
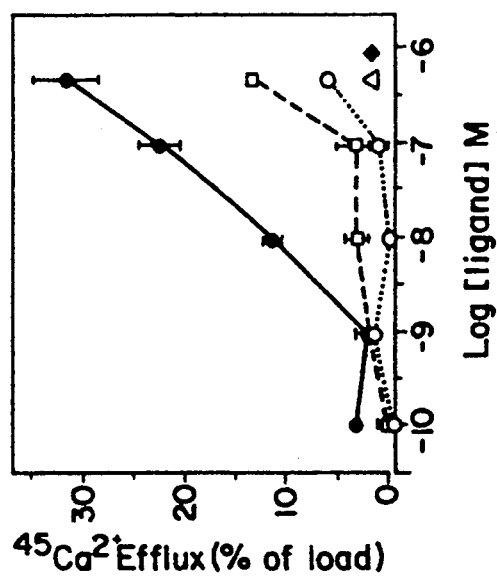

The IL-8 receptor expressed by Xenopus oocytes also activated a calcium flux in response to structurally related ligands with a rank order of potency of IL-8>gro>NAP-2 (FIG. 2(C)). This is identical to the rank order of competition with [$^{125}$I]-IL-8 for binding to neutrophils. See B. Moser, C. Schumacher, V. von Tscharner, I. Clark-Lewis, M. Baggiolini, *J. Biol. Chem.* 266, 10666 (1991). C5a, a structurally unrelated chemoattractant that is similar in size (74 amino acids) and charge (pI 8.6) to IL-8, did not activate the IL-8 receptor (FIG. 2C).

To further support the data obtained from the oocyte studies, the p2 cDNA was also cloned into the vector pCDNAI. When COS cells are transiently transfected with the pCDNAI-p2 construct, specific binding sites were detected with $^{125}$I-labeled IL-8 and gro protein. In contrast to the ligand binding affinity in the oocyte environment, the affinity for the ligand when the receptor encoded by p2 was expressed in the COS cell was higher. Specifically, the $k_d$ for IL-8 was 2 nM and the $k_d$ for gro was 1.3 nM. These results corroborate the data obtained from the oocyte studies, indicating that p2 encodes a receptor for both IL-8 and gro.

Example 4

A p2 probe was hybridized under conditions of high stringency to blots of human genomic DNA. Specifically, human genomic DNA (3 μg per lane) was digested with 6 units of Eco RI, Eco RV, Hind III, Pst I, or Xba I restriction endonucleases (Boehringer-Mannheim, Indianapolis, Ind.) and was then fractionated by electrophoresis on an agarose gel (1%).

Figure 4:
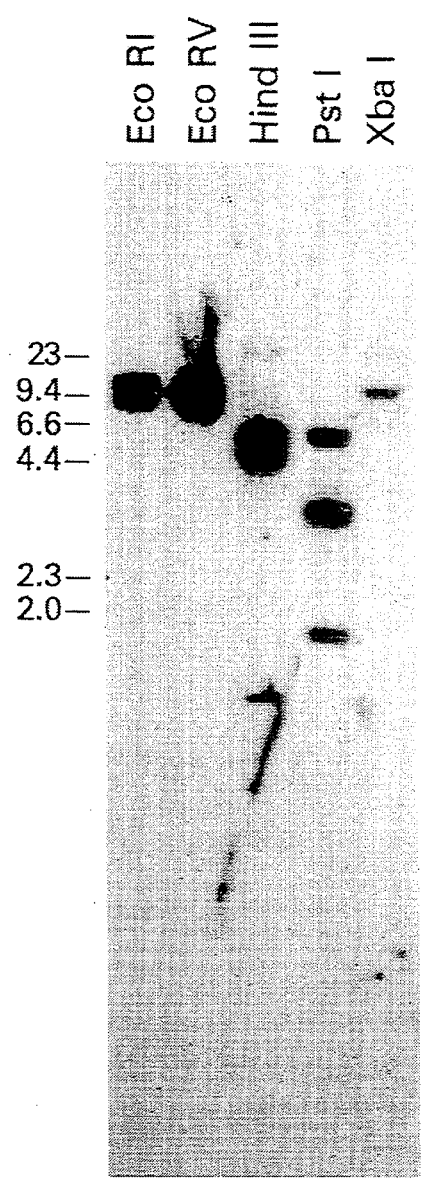
FIG. 4 relates to a genomic analysis of a human IL-8 receptor. A Nytran blot of human genomic DNA digested with the indicated restriction endonucleases was hybridized with full-length cDNA of the IL-8 receptor at high stringency (final wash at 68° C. in 0.1 X SSPE for 1 hour). The blot was exposed to Kodak XAR-2 film in a Quanta III cassette at −80° C. for 5 days. The position of chain length standards is indicated in kilobases at the left. The autoradiogram shown is representative of two independent experiments.

After denaturation in alkaline solution the DNA was transferred to a Nytran filter by capillary action. The banding pattern obtained was most consistent with one copy per haploid genome of a small gene encoding the IL-8 receptor (FIG. 4). Detection of faint bands, however, in DNA digested with Eco RV, Hind III, and Xba I after long exposure of the blot suggested that another human homologue of F3R could be found with the p2 probe. HL60 neutrophil cDNA libraries were therefore rescreened with a p2 probe. Thirteen hybridizing plaques were sequenced; all were identical to p2. Therefore, a gene encoding a receptor more closely related to F3R is expressed either at very low levels, or not at all, in HL60 neutrophils.

Characteristics of various portions of the IL-8 receptor have been established. It has been found that the receptor contains seven hydrophobic segments predicted to span the cell membrane, a characteristic of the superfamily of G protein-coupled receptors (FIGS. 3(A)-3(C)). The COOH-terminal segment contains 11 serine or threonine residues that may be phosphorylation sites for cellular kinases. The 20 amino acid third cytoplasmic loop, which may interact with G proteins, is similar in size to that of other peptide receptors. The IL-8 receptor has a single predicted site for N-linked glycosylation in the $NH_2$-terminal segment and two sites in the second extracellular loop. As with the C5a receptor, the $NH_2$-terminal segment is rich in acidic residues and may form the binding site for IL-8, which is basic (pI~9.5). See N. P. Gerard and C. Gerard, *Nature* 349, 614 (1991).

The IL-8 receptor has been compared with other related receptors. The IL-8 receptor possesses 69% amino acid identity to F3R after the imposition of 10 gaps. If only the predicted transmembrane domains (TMD) are compared, 84% identity is found with F3R. Alignment with ten other G protein-coupled receptor sequences and examination of corresponding DNA sequences indicates that the apparent divergence of the IL-8 receptor from F3R between residues 92 and 105 is due to a frame shift in F3R. See T. I. Bonner, A. C. Young, M. R. Brann, N. J. Buckley, *Neuron* 1, 403 (1988); and S. Yokoyama, K. E. Eisenberg, A. F. Wright, *Mol. Biol. Evol.* 6, 342 (1989). Moderately conserved domains include the $NH_2$-terminal segment (38% identity, 4 gaps), the first extracellular loop (33%, 1 gap) and the COOH-terminal 23 residues (22%, no gaps). The third cytoplasmic loops are 95% identical. The IL-8 receptor possesses less than 30% amino acid identity with all other reported G protein-coupled receptor sequences including that of FPR (FIGS. 3(A)-3(C)).

In a related development, a cDNA from human neutrophils has been found that encodes a distinct IL-8 receptor. This receptor has 77% amino acid identity with the IL-8 receptor encoded by p2, and is more closely related to F3R (SEQ ID NO:1:) (79% versus 69% amino acid identity). Neither human IL-8 receptor interacts with N-formyl peptides. The receptor encoded by p2 diverges most extensively from the other two sequences in the $NH_2$-terminal segment, although the acidic character of this region is conserved. Thus, the human neutrophil expresses at least two distinct calcium mobilizing IL-8 receptors. One of these, that encoded by p2, also is a gro receptor. The ability to bind gro of the other IL-8 receptor, the one more closely related to F3R, is not known. Structural comparison of the human IL-8 receptors with F3R predicts that F3R encodes a high affinity rabbit IL-8 receptor. In fact, to corroborate this prediction, Thomas et al. recently reported that F3R does encode a high affinity rabbit IL-8 receptor (See K. M. Thomas, L. Taylor, J. Navarro, *J. Biol. Chem.*, 266, 14839-14841 (1991)).

While the foregoing invention has been described in some detail for purposes of clarity and understanding, it will be clear to one skilled in the art from a reading of this disclosure that various changes in form and detail can be made without departing from the true scope of the invention. All publications cited in this application are specifically incorporated by reference herein.

---

What is claimed is:

1. An isolated interleukin-8 receptor, wherein said receptor has an amino acid sequence according to SEQ ID NO:1.

2. An interleukin-8 receptor according to claim 1, wherein said receptor is a gro receptor.

3. The receptor of claim 1, wherein said receptor has intracellular calcium mobilizing properties and has IL-8 and gro ligand binding properties.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
(A) LENGTH: 355 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:1:

| Met<br>1 | Glu | Ser | Asp | Ser<br>5 | Phe | Glu | Asp | Phe | Trp<br>10 | Lys | Gly | Glu | Asp | Leu<br>15 | Ser |
|---|---|---|---|---|---|---|---|---|---|---|---|---|---|---|---|
| Asn | Tyr | Ser | Tyr<br>20 | Ser | Ser | Thr | Leu | Pro<br>25 | Pro | Phe | Leu | Leu | Asp<br>30 | Ala | Ala |
| Pro | Cys | Glu<br>35 | Pro | Glu | Ser | Leu | Glu<br>40 | Ile | Asn | Lys | Tyr | Phe<br>45 | Val | Val | Ile |
| Ile | Tyr<br>50 | Ala | Leu | Val | Phe | Leu<br>55 | Leu | Ser | Leu | Leu | Gly<br>60 | Asn | Ser | Leu | Val |
| Met<br>65 | Leu | Val | Ile | Leu | Tyr<br>70 | Ser | Arg | Val | Gly | Arg<br>75 | Ser | Val | Thr | Asp | Val<br>80 |
| Tyr | Leu | Leu | Asn | Leu<br>85 | Ala | Leu | Ala | Asp | Leu<br>90 | Leu | Phe | Ala | Leu | Thr<br>95 | Leu |
| Pro | Ile | Trp | Ala<br>100 | Ala | Ser | Lys | Val | Asn<br>105 | Gly | Trp | Ile | Phe | Gly<br>110 | Thr | Phe |
| Leu | Cys | Lys<br>115 | Val | Val | Ser | Leu | Leu<br>120 | Lys | Glu | Val | Asn | Phe<br>125 | Tyr | Ser | Gly |
| Ile | Leu<br>130 | Leu | Leu | Ala | Cys | Ile<br>135 | Ser | Val | Asp | Arg | Tyr<br>140 | Leu | Ala | Ile | Val |
| His<br>145 | Ala | Thr | Arg | Thr | Leu<br>150 | Thr | Gln | Lys | Arg | Tyr<br>155 | Leu | Val | Lys | Phe | Ile<br>160 |
| Cys | Leu | Ser | Ile | Trp<br>165 | Gly | Leu | Ser | Leu | Leu<br>170 | Leu | Ala | Leu | Pro | Val<br>175 | Leu |
| Leu | Phe | Arg | Arg<br>180 | Thr | Val | Tyr | Ser | Ser<br>185 | Asn | Val | Ser | Pro | Ala<br>190 | Cys | Tyr |
| Glu | Asp | Met<br>195 | Gly | Asn | Asn | Thr | Ala<br>200 | Asn | Trp | Arg | Met | Leu<br>205 | Leu | Arg | Ile |
| Leu | Pro<br>210 | Gln | Ser | Phe | Gly | Phe<br>215 | Ile | Val | Pro | Leu | Leu<br>220 | Ile | Met | Leu | Phe |
| Cys<br>225 | Tyr | Gly | Phe | Thr | Leu<br>230 | Arg | Thr | Leu | Phe | Lys<br>235 | Ala | His | Met | Gly | Gln<br>240 |
| Lys | His | Arg | Ala | Met<br>245 | Arg | Val | Ile | Phe | Ala<br>250 | Val | Val | Leu | Ile | Phe<br>255 | Leu |
| Leu | Cys | Trp | Leu<br>260 | Pro | Tyr | Asn | Leu | Val<br>265 | Leu | Leu | Ala | Asp | Thr<br>270 | Leu | Met |
| Arg | Thr | Gln<br>275 | Val | Ile | Gln | Glu | Thr<br>280 | Cys | Glu | Arg | Arg | Asn<br>285 | His | Ile | Asp |
| Arg | Ala<br>290 | Leu | Asp | Ala | Thr | Glu<br>295 | Ile | Leu | Gly | Ile | Leu<br>300 | His | Ser | Cys | Leu |
| Asn | Pro | Leu | Ile | Tyr | Ala | Phe | Ile | Gly | Gln | Lys | Phe | Arg | His | Gly | Leu |

| | | | | 305 | | | | | 310 | | | | | 315 | | | | | 320 |

Leu Lys Ile Leu Ala Ile His Gly Leu Ile Ser Lys Asp Ser Leu Pro
                    325             330                 335

Lys Asp Ser Arg Pro Ser Phe Val Gly Ser Ser Ser Gly His Thr Ser
            340                 345                 350

Thr Thr Leu
        355

( 2 ) INFORMATION FOR SEQ ID NO:2:

( i ) SEQUENCE CHARACTERISTICS:
        ( A ) LENGTH: 354 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Met Glu Val Asn Val Trp Asn Met Thr Asp Leu Trp Thr Trp Phe Glu
1               5                   10                  15

Asp Glu Phe Ala Asn Ala Thr Gly Met Pro Pro Val Glu Lys Asp Tyr
            20                  25                  30

Ser Pro Cys Leu Val Val Thr Gln Thr Leu Asn Lys Tyr Val Val Val
        35                  40                  45

Val Ile Tyr Ala Leu Val Phe Leu Leu Ser Leu Leu Gly Asn Ser Leu
    50                  55                  60

Val Met Leu Val Ile Leu Tyr Ser Arg Ser Asn Arg Ser Val Thr Asp
65                  70                  75                  80

Val Tyr Leu Leu Asn Leu Ala Met Ala Pro Ala Phe Cys Pro Asp His
                85                  90                  95

Ala Tyr Leu Gly Arg Leu Gln Gly Lys Arg Leu Asp Phe Arg Thr Pro
                100                 105                 110

Leu Cys Lys Val Val Ser Leu Val Lys Glu Val Asn Phe Tyr Ser Gly
            115                 120                 125

Ile Leu Leu Leu Ala Cys Ile Ser Val Asp Arg Tyr Leu Ala Ile Val
    130                 135                 140

Gln Ser Thr Arg Thr Leu Thr Gln Lys Arg His Leu Val Lys Phe Ile
145                 150                 155                 160

Cys Leu Gly Ile Trp Ala Leu Ser Leu Ile Leu Ser Leu Pro Phe Phe
                165                 170                 175

Leu Phe Arg Gln Val Phe Ser Pro Asn Asn Ser Ser Pro Val Cys Tyr
            180                 185                 190

Glu Asp Leu Gly His Asn Thr Ala Lys Trp Cys Met Val Leu Arg Ile
        195                 200                 205

Leu Pro His Thr Phe Gly Phe Ile Leu Pro Leu Leu Val Met Leu Phe
    210                 215                 220

Cys Tyr Gly Phe Thr Leu Arg Thr Leu Phe Gln Ala His Met Gly Gln
225                 230                 235                 240

Lys His Arg Ala Met Arg Val Ile Phe Ala Val Val Leu Ile Phe Leu
                245                 250                 255

Leu Cys Trp Leu Pro Tyr Asn Leu Val Leu Leu Ala Asp Thr Leu Met
            260                 265                 270

Arg Thr His Val Ile Gln Glu Thr Cys Gln Arg Arg Asn Glu Leu Asp
        275                 280                 285

Arg Ala Leu Asp Ala Thr Glu Ile Leu Gly Phe Leu His Ser Cys Leu
    290                 295                 300

Asn Pro Ile Ile Tyr Ala Phe Ile Gly Gln Asn Phe Arg Asn Gly Phe

|     |     |     |     | 305 |     |     |     |     | 310 |     |     |     |     | 315 |     |     |     |     | 320 |
| --- | --- | --- | --- | --- | --- | --- | --- | --- | --- | --- | --- | --- | --- | --- | --- | --- | --- | --- | --- |
| Leu | Lys | Met | Leu | Ala | Ala | Arg | Gly | Leu | Ile | Ser | Lys | Glu | Phe | Leu | Thr |
|     |     |     |     | 325 |     |     |     |     | 330 |     |     |     |     | 335 |     |
| Arg | His | Arg | Val | Thr | Ser | Tyr | Thr | Ser | Ser | Thr | Asn | Val | Pro | Ser |
|     |     |     |     | 340 |     |     |     |     | 345 |     |     |     |     | 350 |     |
| Asn | Leu |

( 2 ) INFORMATION FOR SEQ ID NO:3:

( i ) SEQUENCE CHARACTERISTICS:
        ( A ) LENGTH: 350 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

| Met | Glu | Thr | Asn | Ser | Ser | Leu | Pro | Thr | Asn | Ile | Ser | Gly | Gly | Thr | Pro |
| --- | --- | --- | --- | --- | --- | --- | --- | --- | --- | --- | --- | --- | --- | --- | --- |
| 1 |   |   |   | 5 |   |   |   |   | 10 |   |   |   |   | 15 |   |
| Ala | Val | Ser | Ala | Gly | Tyr | Leu | Phe | Leu | Asp | Ile | Ile | Thr | Tyr | Leu | Val |
|   |   |   |   | 20 |   |   |   |   | 25 |   |   |   |   | 30 |   |
| Phe | Ala | Val | Thr | Phe | Val | Leu | Gly | Val | Leu | Gly | Asn | Gly | Leu | Val | Ile |
|   |   |   |   | 35 |   |   |   |   | 40 |   |   |   |   | 45 |   |
| Trp | Val | Ala | Gly | Phe | Arg | Met | Thr | His | Thr | Val | Thr | Thr | Ile | Ser | Tyr |
|   |   |   |   | 50 |   |   |   |   | 55 |   |   |   |   | 60 |   |
| Leu | Asn | Leu | Ala | Val | Ala | Asp | Phe | Cys | Phe | Thr | Ser | Thr | Leu | Pro | Phe |
| 65 |   |   |   |   |   | 70 |   |   |   |   | 75 |   |   |   | 80 |
| Phe | Met | Val | Arg | Lys | Ala | Met | Gly | Gly | His | Trp | Pro | Phe | Gly | Trp | Phe |
|   |   |   |   | 85 |   |   |   |   | 90 |   |   |   |   | 95 |   |
| Leu | Cys | Lys | Phe | Leu | Phe | Thr | Ile | Val | Asp | Ile | Asn | Leu | Phe | Gly | Ser |
|   |   |   |   | 100 |   |   |   |   | 105 |   |   |   |   | 110 |   |
| Val | Phe | Leu | Ile | Ala | Leu | Ile | Ala | Leu | Asp | Arg | Cys | Val | Cys | Val | Leu |
|   |   |   |   | 115 |   |   |   |   | 120 |   |   |   |   | 125 |   |
| His | Pro | Val | Trp | Thr | Gln | Asn | His | Arg | Thr | Val | Ser | Leu | Ala | Lys | Lys |
|   |   |   |   | 130 |   |   |   |   | 135 |   |   |   |   | 140 |   |
| Val | Ile | Ile | Gly | Pro | Trp | Val | Met | Ala | Leu | Leu | Leu | Thr | Leu | Pro | Val |
| 145 |   |   |   |   |   | 150 |   |   |   |   | 155 |   |   |   | 160 |
| Ile | Ile | Arg | Val | Thr | Thr | Val | Pro | Gly | Lys | Thr | Gly | Thr | Val | Ala | Cys |
|   |   |   |   | 165 |   |   |   |   | 170 |   |   |   |   | 175 |   |
| Thr | Phe | Asn | Phe | Ser | Pro | Trp | Thr | Asn | Asp | Pro | Lys | Glu | Arg | Ile | Asn |
|   |   |   |   | 180 |   |   |   |   | 185 |   |   |   |   | 190 |   |
| Val | Ala | Val | Ala | Met | Leu | Thr | Val | Arg | Gly | Ile | Ile | Arg | Phe | Ile | Ile |
|   |   |   |   | 195 |   |   |   |   | 200 |   |   |   |   | 205 |   |
| Gly | Phe | Ser | Ala | Pro | Met | Ser | Ile | Val | Ala | Val | Ser | Tyr | Gly | Leu | Ile |
|   |   |   |   | 210 |   |   |   |   | 215 |   |   |   |   | 220 |   |
| Ala | Thr | Lys | Ile | His | Lys | Gln | Gly | Leu | Ile | Lys | Ser | Ser | Arg | Pro | Leu |
| 225 |   |   |   |   |   | 230 |   |   |   |   | 235 |   |   |   | 240 |
| Arg | Val | Leu | Ser | Phe | Val | Ala | Ala | Ala | Phe | Phe | Leu | Cys | Trp | Ser | Pro |
|   |   |   |   | 245 |   |   |   |   | 250 |   |   |   |   | 255 |   |
| Tyr | Gln | Val | Val | Ala | Leu | Ile | Ala | Thr | Val | Arg | Ile | Arg | Glu | Leu | Leu |
|   |   |   |   | 260 |   |   |   |   | 265 |   |   |   |   | 270 |   |
| Gln | Gly | Met | Tyr | Lys | Glu | Ile | Gly | Ile | Ala | Val | Asp | Val | Thr | Ser | Ala |
|   |   |   |   | 275 |   |   |   |   | 280 |   |   |   |   | 285 |   |
| Leu | Ala | Phe | Phe | Asn | Ser | Cys | Leu | Asn | Pro | Met | Leu | Tyr | Val | Phe | Met |
|   |   |   |   | 290 |   |   |   |   | 295 |   |   |   |   | 300 |   |
| Gly | Gln | Asp | Phe | Arg | Glu | Arg | Leu | Ile | His | Ala | Leu | Pro | Ala | Ser | Leu |
| 305 |   |   |   |   |   | 310 |   |   |   |   | 315 |   |   |   | 320 |

|     |     |     |     |     |     |     |     |     |     |     |     |     |     |
| --- | --- | --- | --- | --- | --- | --- | --- | --- | --- | --- | --- | --- | --- |
| Glu | Arg | Ala | Leu | Thr | Glu | Asp | Ser | Thr | Gln | Thr | Ser | Asp | Thr | Ala | Thr |
|     |     |     |     | 325 |     |     |     | 330 |     |     |     |     | 335 |

| Asn | Ser | Thr | Leu | Pro | Ser | Ala | Glu | Val | Ala | Leu | Gln | Ala | Lys |
|     |     |     | 340 |     |     |     |     | 345 |     |     |     | 350 |

( 2 ) INFORMATION FOR SEQ ID NO:4:

( i ) SEQUENCE CHARACTERISTICS:
        ( A ) LENGTH: 1510 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

| | | | | | |
|---|---|---|---|---|---|
| GTCAGGATTT | AAGTTTACCT | CAAAAATGGA | AGATTTTAAC | ATGGAGAGTG | ACAGCTTTGA | 60 |
| AGATTTCTGG | AAAGGTGAAG | ATCTTAGTAA | TTACAGTTAC | AGCTCTACCC | TGCCCCCTTT | 120 |
| TCTACTAGAT | GCCGCCCCAT | GTGAACCAGA | ATCCCTGGAA | ATCAACAAGT | ATTTTGTGGT | 180 |
| CATTATCTAT | GCCCTGGTAT | TCCTGCTGAG | CCTGCTGGGA | AACTCCCTCG | TGATGCTGGT | 240 |
| CATCTTATAC | AGCAGGGTCG | GCCGCTCCGT | CACTGATGTC | TACCTGCTGA | ACCTAGCCTT | 300 |
| GGCCGACCTA | CTCTTTGCCC | TGACCTTGCC | CATCTGGGCC | GCCTCAAGG | TGAATGGCTG | 360 |
| GATTTTTGGC | ACATTCCTGT | GCAAGGTGGT | CTCACTCCTG | AAGGAAGTCA | ACTTCTATAG | 420 |
| TGGCATCCTG | CTACTGGCCT | GCATCAGTGT | GGACCGTTAC | CTGGCCATTG | TCCATGCCAC | 480 |
| ACGCACACTG | ACCCAGAAGC | GCTACTTGGT | CAAATTCATA | TGTCTCAGCA | TCTGGGGTCT | 540 |
| GTCCTTGCTC | CTGGCCCTGC | CTGTCTTACT | TTTCCGAAGG | ACCGTCTACT | CATCCAATGT | 600 |
| TAGCCCAGCC | TGCTATGAGG | ACATGGGCAA | CAATACAGCA | AACTGGCGGA | TGCTGTTACG | 660 |
| GATCCTGCCC | CAGTCCTTTG | GCTTCATCGT | GCCACTGCTG | ATCATGCTGT | TCTGCTACGG | 720 |
| ATTCACCCTG | CGTACGCTGT | TTAAGGCCCA | CATGGGGCAG | AAGCACCGGG | CCATGCGGGT | 780 |
| CATCTTTGCT | GTCGTCCTCA | TCTTCCTGCT | TTGCTGGCTG | CCCTACAACC | TGGTCCTGCT | 840 |
| GGCAGACACC | CTCATGAGGA | CCCAGGTGAT | CCAGGAGACC | TGTGAGCGCC | GCAATCACAT | 900 |
| CGACCGGGCT | CTGGATGCCA | CCGAGATTCT | GGGCATCCTT | CACAGCTGCC | TCAACCCCCT | 960 |
| CATCTACGCC | TTCATTGGCC | AGAAGTTTCG | CCATGGACTC | CTCAAGATTC | TAGCTATACA | 1020 |
| TGGCTTGATC | AGCAAGGACT | CCCTGCCCAA | AGACAGCAGG | CCTTCCTTTG | TTGGCTCTTC | 1080 |
| TTCAGGGCAC | ACTTCCACTA | CTCTCTAAGA | CCTCCTGCCT | AAGTGCAGCC | CGTGGGGTTC | 1140 |
| CTCCCTTCTC | TTCACAGTCA | CATTCCAAGC | CTCATGTCCA | CTGGTTCTTC | TTGGTCTCAG | 1200 |
| TGTCAATGCA | GCCCCCATTG | TGGTCACAGG | AAGCAGAGGA | GGCCACGTTC | TTACTAGTTT | 1260 |
| CCCTTGCATG | GTTTAGAAAG | CTTGCCCTGG | TGCCTCACCC | CTTGCCATAA | TTACTATGTC | 1320 |
| ATTTGCTGGA | GCTCTGCCCA | TCCTGCCCCT | GAGCCCATGG | CACTCTATGT | TCTAAGAAGT | 1380 |
| GAAAATCTAC | ACTCCAGTGA | GACAGCTCTG | CATACTCATT | AGGATGGCTA | GTATCAAAAG | 1440 |
| AAAGAAAATC | AGGCTGGCCA | ACGGGATGAA | ACCCTGTCTC | TACTAAAAAT | ACAAAAAAAA | 1500 |
| AAAAAAAAAA | | | | | | 1510 |

( 2 ) INFORMATION FOR SEQ ID NO:5:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

GACGTCTACC TGCTGAACCT GGCCATGGCA CCTGCTTTT 39